US00PP31484P2

(12) United States Plant Patent
Hansen

(10) Patent No.: US PP31,484 P2
(45) Date of Patent: Feb. 25, 2020

(54) ***PHLOX* PLANT NAMED 'EYE CANDY'**

(50) Latin Name: *Phlox subulata*
Varietal Denomination: Eye Candy

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,912

(22) Filed: Feb. 1, 2019

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A unique cultivar of Hybrid Spring *Phlox* named *Phlox* 'Eye Candy' characterized by multi-stemmed compact habit, winter-hardy, spreading plant with short, bright glossy-green, awl-shaped leaves. Flowering begins in mid-April and continuing for nearly five weeks on lightly branched peduncles and completely cover the plant in peak season. Petals are light lavender-pink with a large pronounced eye of dark wine purple. Petal apices are shallowly notched. Foliage stays clean and resists mildew, and the new plant is especially suitable for the landscape as a potted plant and in the garden as a specimen or en masse.

1 Drawing Sheet

Botanical classification: *Phlox subulata.*
Variety denomination: 'Eye Candy'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2018. The claimed plant was first sold on Jul. 9, 2018 by Walters Gardens, Inc., who obtained the plant and all information relating thereto, from the inventor. No plants of *Phlox* 'Eye Candy' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Eye Candy' and will be referred to hereafter by its cultivar name, 'Eye Candy', or the "new plant". The new plant was hybridized at a wholesale perennial nursery in Zeeland, Mich. on Apr. 18, 2013 as cross between *Phlox subulata* 'North Hills' (not patented) as the female parent times *Phlox subulata* 'Emerald Pink' (not patented) as the male parent. The new plant was passed initial evaluation on the spring of 2015 and was assigned the breeder code 13-66-1 through the remaining evaluation process. 'Eye Candy' was first asexually propagated by stem cuttings in the greenhouses at the same nursery in Zeeland, Mich. in the summer of 2015. The unique characteristics of the new plant have been found to be reproducible and stable in successive generations of asexually propagated and the resultant plants have been found to be identical to the original selection.

BRIEF SUMMARY OF THE PLANT

*Phlox* 'Eye Candy' is unique from all other Creeping *Phlox* known to the inventor. The nearest comparison plants known to the inventor include: 'Blue Emerald' (not patented), 'Red Wing' (not patented) and the copending cultivar 'Eye Shadow' U.S. Pat. No. 31,169. 'Blue Emerald' has flowers of a delicate lavender-blue. 'Red Wing' has flowers of bright crimson-pink. The female parent, 'North Hills' has flowers that are bright white with prominent violet purple eye. The male parent, 'Emerald Pink' has flowers that are pink without a prominent dark eye, for a shorter season.

*Phlox* 'Eye Candy' differs from and all other *phlox* known to the inventor in the following repeatedly observed traits in combination:

1. Plants of compact habit, spreading by rooting stems, producing short, clean, glossy, bright-green, awl-shaped leaves.
2. Multiple heavily-branched stems produce lightly branched panicles.
3. Flower beginning in mid-April and continuing for nearly five weeks completely covering plant at peak flowering.
4. Flowers of light lavender-pink with dark wine-purple eye;

BRIEF DESCRIPTION OF THE DRAWINGS

The photographs of the new plant demonstrate the unique traits of *Phlox* 'Eye Candy' and the overall appearance of the plant at three-years old growing in a full-sun trial bed in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
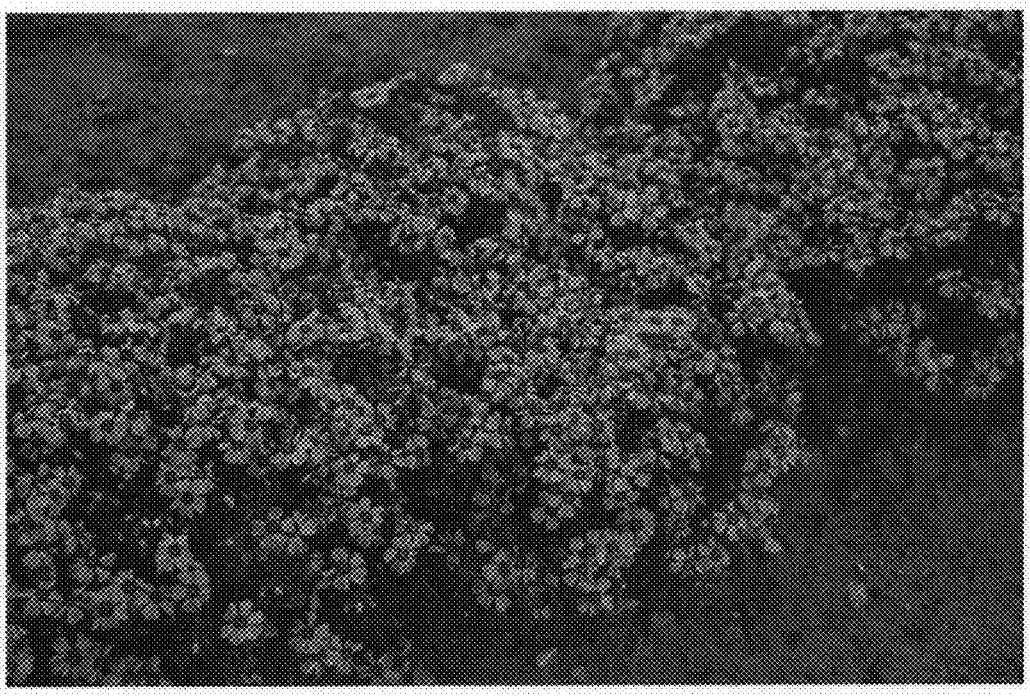
FIG. 1 shows the new plant in peak flower in the landscape.
Figure 2:
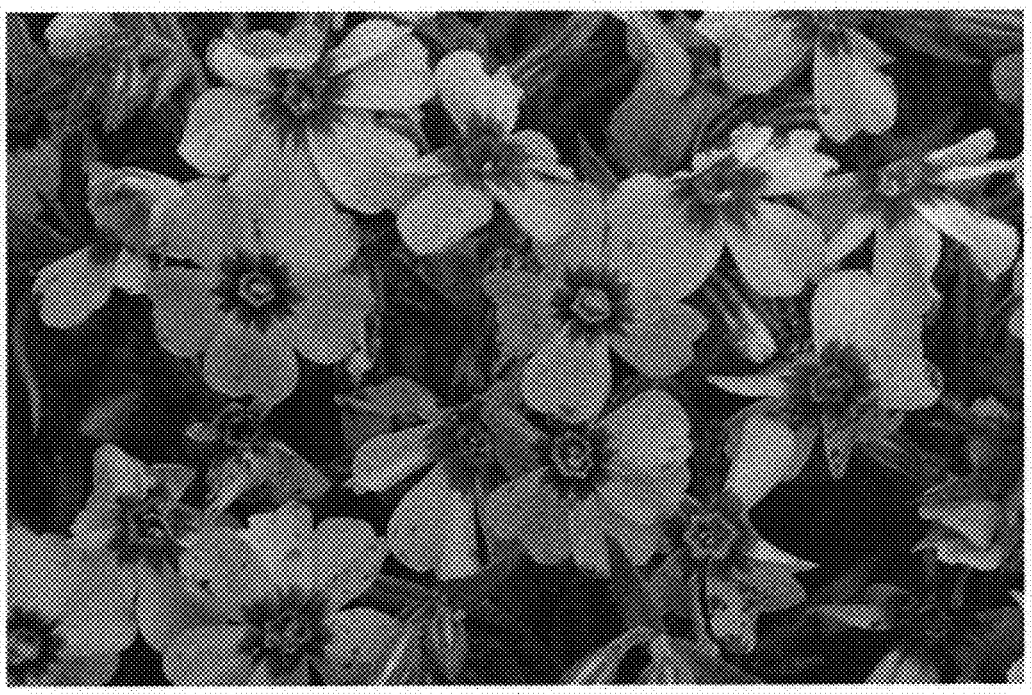
FIG. 2 shows a close-up of the flowers and buds.

The following descriptions and color references are based on the 2015 edition of The Royal Horticultural Society Colour Chart except where common dictionary terms are used. *Phlox* 'Eye Candy' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox subulata;*

Parentage: Female or seed parent is *Phlox subulata* 'North Hills', male or pollen parent is *Phlox subulata* 'Emerald Pink';

Plant habit: Winter-hardy, evergreen herbaceous perennial; compact, highly branched; producing about 50 to 75 stiff, highly-branched stems; foliage 18.0 cm tall and 77.0 cm wide, average 16.5 cm tall and 73.0 cm wide; flowering to 20.0 cm tall and 78.0 cm wide;

Propagation: Stem cuttings; rooting in about 3 weeks;

Time to produce finished crop in 3.8 liter pots: About 6 to 9 weeks; vigorous;

Root: Fibrous and freely branching; color creamy white to tan depending on soil type;

Leaves: Simple; alternate proximally, whorled distally; linear to subulate; apex apiculate; base truncate, clasping; margin entire, micro-ciliolate; lustrous and glabrous both adaxial and abaxial; about 19.0 mm long by about 2.0 mm wide;

Leaf color: Adaxial expanding and mature nearest RHS 138A; abaxial expanding and mature nearest RHS 146B;

Foliage fragrance: None detected;

Veins: Pinnate; not conspicuous adaxial and abaxial;

Vein color: Same color as surround leaf;

Petiole: Leaves sessile;

Stems: Cylindrical; stiff; twisting; wiry; to 1.5 mm diameter and branching at nearly every node; internodes about 5.0 mm long; strong; upright; covered in leaves distally; about 16.0 mm long and 1.5 mm diameter at base;

Stem color: Nearest RHS 199D;

Nodes: Proximally about 5.0 mm apart; distally less than 1.0 mm apart;

Node color: Same as surrounding stem;

Flowers: Perfect; salverform; slightly reflexed; about 17.0 mm across the flat face and 17.0 mm long; with fused corolla tube about 13.0 mm long and 2.0 mm diameter near face; in branched panicle of about 3 to 4 flowers; attitude upright to outwardly;

Flower longevity: About 5 days on plant; self-cleaning;

Flower fragrance: Pleasantly sweet;

Buds one to two days prior to opening: Narrowly oblanceolate, to narrowly clavate; acute apex with petals implicate; about 19.0 mm long, 5.5 mm long in terminal bulb portion and 13.5 mm long in tube; tube to 2.0 mm diameter;

Bud color: Nearest RHS 77D in distal bulb portion, exposed tube nearest RHS N77D and 0.5 mm ring between bulb and tube nearest RHS N77A;

Petals: Five; glabrous; cleft blade and claw base fused into tube; apex emarginate less than 1.0 mm deep; blades rarely imbricate; glabrous adaxial and abaxial except adaxial 1.0 mm section about 2.0 mm from base;

Petal size: Blade about 9.0 mm long and 8.0 mm wide near center; tube about 13.0 mm long and 2.0 mm diameter;

Petal color:

Young adaxial: Basal 2.0 mm of tube nearest RHS 145D, tube lighter than RHS 77D, blade center nearest RHS N78C with 2.0 mm eye nearest blend of RHS 71A and RHS N79C, distal blade nearest RHS 77C;

Young abaxial: Basal tube 2.0 mm nearest RHS 145D, distal tube nearest RHS N77D and lighter than RHS N77D just before blade; blade nearest RHS 76B;

Mature adaxial: Basal 2.0 mm of tube nearest RHS 145C, tube nearest RHS 76B, center blade nearest RHS 76D with 2.0 mm eye of nearest RHS N79C, distal blade nearest RHS 76B;

Mature abaxial: Basal 2.0 mm of tube nearest RHS145C, distal tube between RHS N77D or lighter than RHS N77D, blade nearest RHS 76C;

Androecium: Typically five;

Filaments: Typically five, adnate to inner corolla at various heights; about 1.0 mm long and 0.1 mm in diameter; color nearest RHS NN155D;

Anther: Oblong elliptic; dorsifixed; oblong, about 2.0 mm long by 0.7 mm wide; color nearest RHS 12C;

Pollen: Nearly microscopic, spherical; color nearest RHS 12C;

Gynoecium: One pistil per flower; 12.0 mm long;

Style: Cylindrical; about 11.0 mm long and 0.2 mm diameter when flower is mature; persistent after flower abscission; color nearest RHS 157D;

Stigma: Trifid in proximal 1.0 mm long, about 0.2 mm diameter; nearest RHS 1C;

Ovary: Inferior; globose, rounded to slightly obtuse apex and truncate base; about 1.2 mm long and 1.0 mm diameter; color nearest RHS 144A;

Calyx: Campanulate; pubescent abaxial, glabrous adaxial; about 7.5 mm long and 2.5 mm across at apex;

Sepals: Five; linear; glabrous; narrowly acute apex, fused in basal 3.0 mm; margin entire; pubescent abaxial, glabrous and lustrous adaxial; individually about 7.5 mm long and 1.0 mm wide at fusion;

Sepal color: Adaxial between RHS 147A and RHS 146A, abaxial nearest RHS 137A with light blush of nearest RHS N186C;

Peduncle: Finely puberulent; strong, flexible; upright to outwardly, cylindrical; about 1.5 mm diameter at base and 1.5 cm long;

Peduncle color: Proximally nearest RHS 145D, distally nearest RHS 147C lightly blushed with RHS 182B;

Pedicle: Cylindrical; finely puberulent; flexible; upright to outwardly; to about 5.0 mm long and 1.0 mm diameter;

Pedicle color: 147C lightly blushed with RHS 182B;

Fruit and seeds: Not yet been observed;

Hardiness and culture: the new plant grows best with plenty of moisture and adequate drainage; hardy to at least from USDA zone 2 through 9.

Disease and pest resistance: *Phlox* 'Eye Candy' demonstrates excellent powdery mildew resistance under conditions that would normally show symptoms.

I claim:

1. A new and distinct cultivar of Creeping *Phlox* plant named *Phlox* 'Eye Candy' as herein described and illustrated.

* * * * *